(12) United States Patent
Wright (10) Patent No.: US 8,833,556 B2
(45) Date of Patent: Sep. 16, 2014

(54) SUCTION TIP HOLSTER INSERT (76) Inventor: Clifford A. Wright, San Diego, CA (US)

(*) Notice: Subject to any disclaimer, the term of this patent is extended or adjusted under 35 U.S.C. 154(b) by 0 days.

(21) Appl. No.: 11/679,445

(22) Filed: Feb. 27, 2007

(65) Prior Publication Data

US 2007/0199846 A1     Aug. 30, 2007

Related U.S. Application Data (63) Continuation-in-part of application No. 11/073,409, filed on Mar. 4, 2005, now abandoned.

(51) Int. Cl.
*B65D 85/30* (2006.01)
*A61M 1/00* (2006.01)

(52) U.S. Cl.
CPC ........... *A61M 1/008* (2013.01); *A61M 2209/06* (2013.01)
USPC ............................ 206/363; 206/305; 220/751

(58) Field of Classification Search
USPC ......... 206/306, 305, 514, 515, 519, 520, 570, 206/478, 480, 518, 438, 363; 220/751, 737, 220/675, 670, 669; 224/666, 667, 668, 224/148.4, 148.7, 268, 269
See application file for complete search history.

(56) References Cited

U.S. PATENT DOCUMENTS

| | | | |
|---|---|---|---|
| 2,522,381 A | 9/1950 | Kramer | |
| 2,994,457 A * | 8/1961 | Fornas | 206/507 |
| 3,275,180 A * | 9/1966 | Optner et al. | 206/521 |
| 3,388,705 A | 6/1968 | Grosshandler | |
| 3,819,081 A * | 6/1974 | Runte | 220/23.87 |
| 3,826,358 A * | 7/1974 | Butler et al. | 206/204 |
| 4,050,466 A * | 9/1977 | Koerbacher | 128/207.14 |
| 4,061,226 A * | 12/1977 | Essen | 206/306 |
| 4,094,641 A * | 6/1978 | Friswell | 436/180 |
| 4,439,884 A | 4/1984 | Giorni | |
| 4,748,007 A | 5/1988 | Gaudion et al. | |
| 4,761,379 A * | 8/1988 | Williams et al. | 600/573 |
| 4,813,538 A | 3/1989 | Blackman | |
| 4,921,488 A | 5/1990 | Maitz et al. | |
| 5,002,534 A | 3/1991 | Rosenblatt | |
| 5,038,766 A | 8/1991 | Parker | |
| 5,062,835 A | 11/1991 | Maitz et al. | |
| 5,183,467 A | 2/1993 | Mouney | |
| 5,316,146 A * | 5/1994 | Graff | 206/438 |
| 5,333,607 A | 8/1994 | Kee et al. | |
| 5,375,711 A | 12/1994 | Bree et al. | |
| 5,454,131 A | 10/1995 | Mackenzie | |
| 5,471,706 A | 12/1995 | Wallock et al. | |
| 5,590,782 A * | 1/1997 | Haber et al. | 206/528 |
| 5,634,569 A * | 6/1997 | DeCoster | 220/735 |
| 5,752,286 A | 5/1998 | Wright | |
| D405,531 S | 2/1999 | Bonds | |
| 5,915,583 A | 6/1999 | Cloonan et al. | |
| 5,945,075 A * | 8/1999 | Chiron et al. | 422/300 |
| 6,183,133 B1 | 2/2001 | Roegner | |

(Continued)

*Primary Examiner* — Steven A. Reynolds
(74) *Attorney, Agent, or Firm* — Fred C. Hernandez; Mintz Levin Cohn Ferris Glovsky and Popeo, P.C.

(57) ABSTRACT

A cleaning and storage holster or insert for a body cavity aspirator instrument includes a substantially longitudinal body defining an interior for receiving the instrument. The body includes a distal region having a closed end portion and a proximal region having an opening for receiving the instrument. An instrument support is included in the distal region for supporting the instrument in a position above the closed end portion.

8 Claims, 7 Drawing Sheets

(56) References Cited

U.S. PATENT DOCUMENTS

| | | | |
|---|---|---|---|
| 6,299,116 B1 * | 10/2001 | Levesque | 248/312.1 |
| 6,585,210 B1 * | 7/2003 | Lee | 248/314 |
| 7,712,622 B2 * | 5/2010 | Ruccolo | 220/23.87 |
| 2002/0172257 A1 * | 11/2002 | Walls et al. | 374/158 |
| 2005/0194507 A1 * | 9/2005 | White | 248/314 |

* cited by examiner

SUCTION TIP HOLSTER INSERT

PRIORITY CLAIM

This Application is a Continuation-In-Part of U.S. patent application Ser. No. 11/073,409, filed Mar. 4, 2005 now abandoned, which is incorporated herein by reference.

TECHNICAL FIELD

The present invention relates in general to a cleaning and storage system for an aspirator instrument. The present invention more particularly relates to a cleaning and storage system for a body cavity aspirator instrument which facilitates the storage of a body cavity aspirator instrument when not in use and which further facilitates the cleaning of the body cavity aspirator instrument prior to its use by a patient as well as sanitary storage of the instrument after its use.

BACKGROUND

For many patient care applications, bodily fluids, such as mucus fluids and meconium fluids, as well as other potentially harmful bodily fluids, must be removed from a patient and disposed of in a safe and efficient manner. In this regard, there have been many different types and kinds of aspirator instruments, devices and tools for moving bodily fluids by suction or vacuum processes.

Various aspirator instruments are configured for removing certain types of bodily fluids from specific body cavities. For example, certain aspirator instruments are configured to dislodge and remove secretions, mucus, and debris from a nasal passageway of a user or patient, while other aspirator devices are configured to remove meconium or mucus fluids from a stomach or lung cavity during delivery of an infant. These aspirator instruments are configured in various shapes, depending on their intended use and more specifically on the shape of the body cavity holding the bodily fluids to be removed.

Because the removal of mucus fluids from the mouth and throat of patients confined in a primary care facility, such as a hospital facility, is such a common requirement in patient care, most, if not all, primary care facilities are equipped with bedside access control consoles. Such access control consoles provide primary care givers immediate access to gases, monitoring equipment, and suction/vacuum/water sources for patient care and treatment.

U.S. Pat. No. 5,002,534, which is incorporated herein by reference, describes in detail the typical use of such an oral aspirator instrument. The aspirator instrument is attached to the neck of a patient using a cord so that a mouthpiece or Yankauer tip instrument can be easily inserted into the mouth of the patient for drawing mucus and other fluids from the body cavity of the patient.

While such an arrangement may have been satisfactory for some applications, it has proven to be less than satisfactory in that a health care provider when not using the aspirator is compelled to either remove the aspirator instrument from the aspirator or lay the instrument with the vacuum tube attached thereon on the patient or the bed of the patient. Thus, if the instrument has been in use, residual body fluids may contaminate the patient or the bed of the patient creating an unwanted and undesired health risk due to the presence of undesirable bacteria and harmful bodily fluids.

Conversely, if the user desires to maintain a safe, clean environment, the aspirator must be utilized promptly so that the Yankauer instrument can be removed and immediately disposed of or alternately removed and placed in a proper container for cleaning and sterilization purposes.

While such a procedure can be followed for minimizing the creation of unwanted and undesired health risks, it is very expensive and time consuming, particularly where a patient must have his or her mouth and throat cleared on a regular and short term or elapsed time basis.

Another problem associated with prior known aspirator systems when utilized on a regular short elapsed time basis is associated with the accumulation of residual mucus fluids in and on the Yankauer tip when the vacuum or suction is terminated. In this regard, in many aspirator systems, when the body cavity aspirator instrument is removed from the mouth of the patient the suction operation is substantially diminished permitting any fluids remaining in the body cavity instrument to be trapped within the tip or end of the instrument and tubing connected to the aspirator.

Some of these problems have been considered and addressed by U.S. Pat. No. 5,752,286 ("the '286 patent"), which is incorporated herein by reference. The '286 patent describes a cleaning and storage system for a body cavity aspirator instrument. The system includes a holder for receiving an aspirator instrument for temporary storage purposes between periods of non-use. A wiper cap disposed over the mouth of the holder helps wipe the instrument of residual fluids when being inserted and removed from the holder. An inlet near the bottom of the holder permits the admittance of a cleaning agent to periodically clean the instrument.

While such an arrangement has solved many of the problems associated with the use of aspirator instruments in cleanroom environments, increased concern about hospital sterilization, in conjunction with the rising costs of healthcare and healthcare equipment, has necessitated further improvements. The '286 patent requires that the holder be cleaned periodically in order to maintain sanitary conditions for its continued use. That notwithstanding, it has been found that after a certain period of time, depending on the frequency of use, cleaning is insufficient to maintain sanitary conditions and the entire holder must be replaced. Given the costs associated with replacing the entire holder, it would be desirable to find a solution that would obviate the need to replace the holder while maintaining sanitary conditions that are appropriate for hospital and clinical use.

SUMMARY

A cleaning and storage holster or insert for a body cavity aspirator instrument includes a substantially longitudinal body defining an interior for receiving the instrument. The body includes a distal region having a closed end portion and a proximal region having an opening for receiving the instrument. An instrument support is included in the distal region for supporting the instrument in a position above the closed end portion.

Other features and advantages of the invention will appear hereinafter. The features of the invention described above can be used separately or together, or in various combinations of one or more of them. The invention resides as well in subcombinations of the features described.

BRIEF DESCRIPTION OF THE DRAWINGS

These and other features and advantages will be apparent from the following more particular description thereof, presented in conjunction with the following drawings, wherein.

DETAILED DESCRIPTION

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below. Any terminology intended to be interpreted in any restricted manner, however, will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

Figure 1:
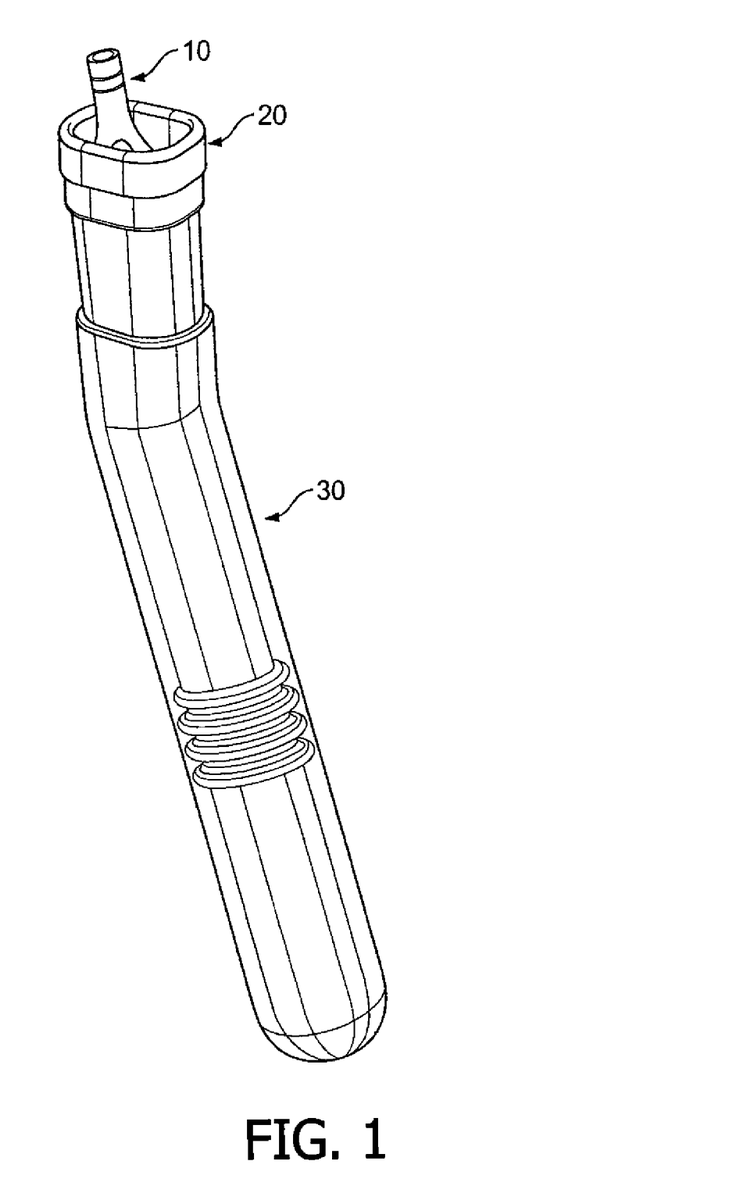
FIG. 1 depicts a three-dimensional view of a cleaning and storage system for a body cavity aspirator instrument in accordance with one embodiment.
Figure 2:
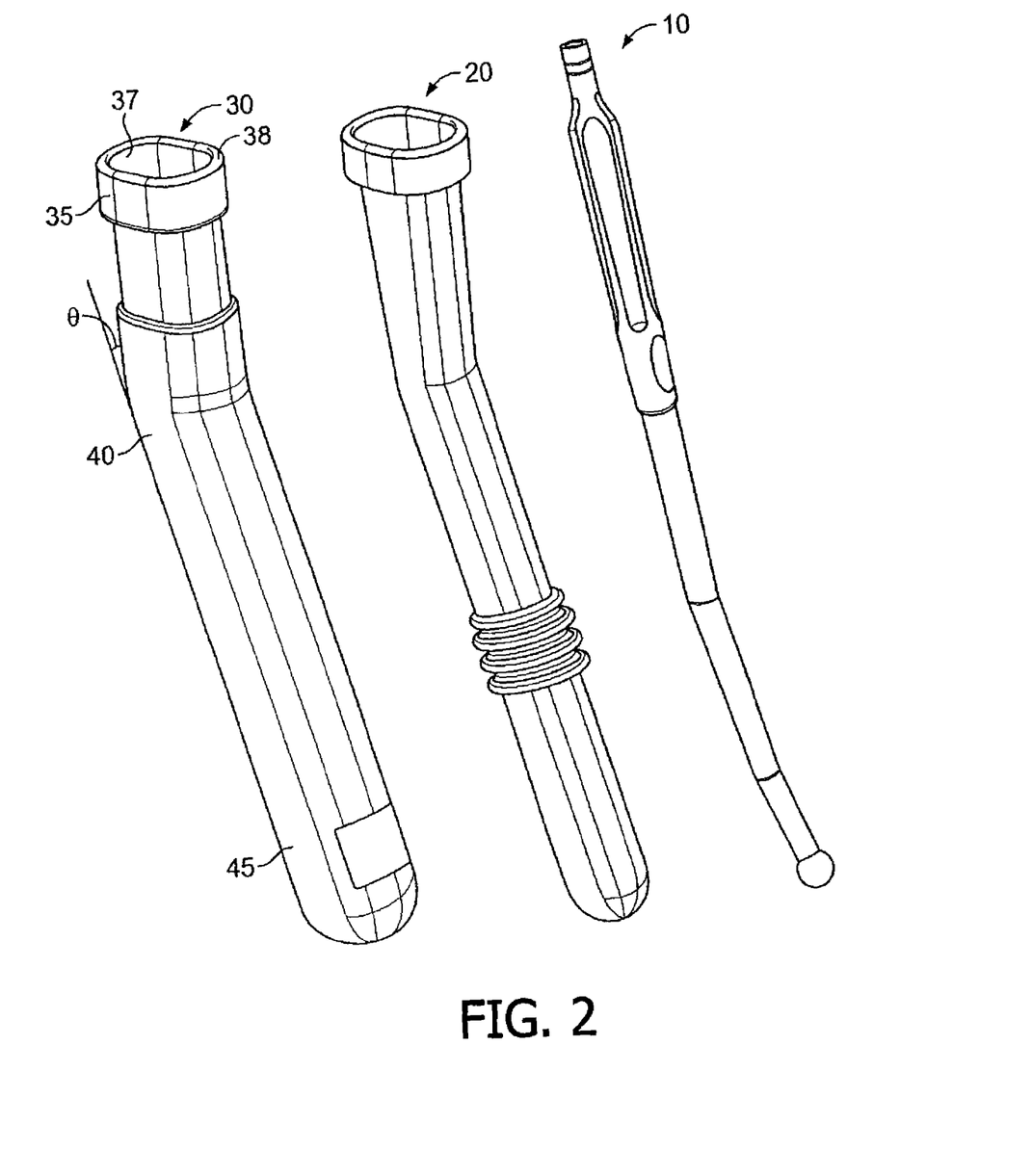
FIG. 2 is an exploded view of the cleaning and storage system depicted in FIG. 1.

Referring now to the drawings, and more particularly to FIGS. 1 and 2 thereof, there is illustrated a cleaning and storage system for a body cavity aspirator instrument, according to one embodiment. The system includes a hollow holder 30 that can be formed of a moldable plastic material. The system further includes a removable and disposable insert 20 that fits within the hollow section of the hollow holder 30. The holder 30 and disposable insert 20 make up the cleaning and storage system for a body cavity aspirator instrument 10, which is also depicted in FIGS. 1 and 2.

The holder 30 has three regions or ends: a proximal region 35; a medial region 40; and a distal region 45. The proximal region 35 forms an opening 37 that receives the disposable insert 20. The medial region 40 forms a transition between the proximal and distal regions. While the holder 30 is substantially longitudinal, the medial region 40 may form a bend that results in the proximal region 35 being at an angle θ relative to the distal region 45. In other words, a longitudinal axis of the proximal region 35 is at an angle θ relative to the longitudinal axis of the distal region 45. The angle θ can be designed to be substantially complementary to a given type of aspirator instrument, such as the Yankauer tip mouthpiece instrument 10. In one embodiment, the angle θ is between about 0 degrees and about 12 degrees. In another embodiment, the angle θ is between about 12 degrees and about 16 degrees. In another embodiment, the angle θ is between about 13 degrees and about 15 degrees. In another embodiment, the angle θ is about 14 degrees. In another embodiment, the angle θ is greater than 16 degrees.

Figure 3:
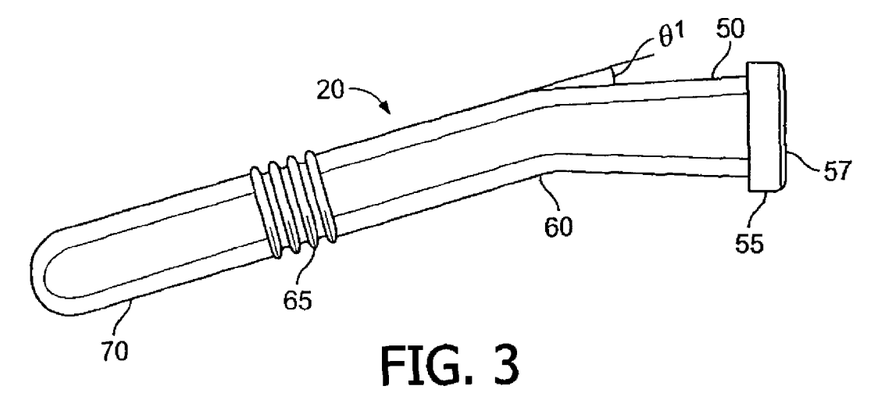
FIG. 3 is longitudinal view of a disposable insert for a cleaning and storage system for a body cavity aspirator instrument in accordance with one embodiment.
Figure 4:
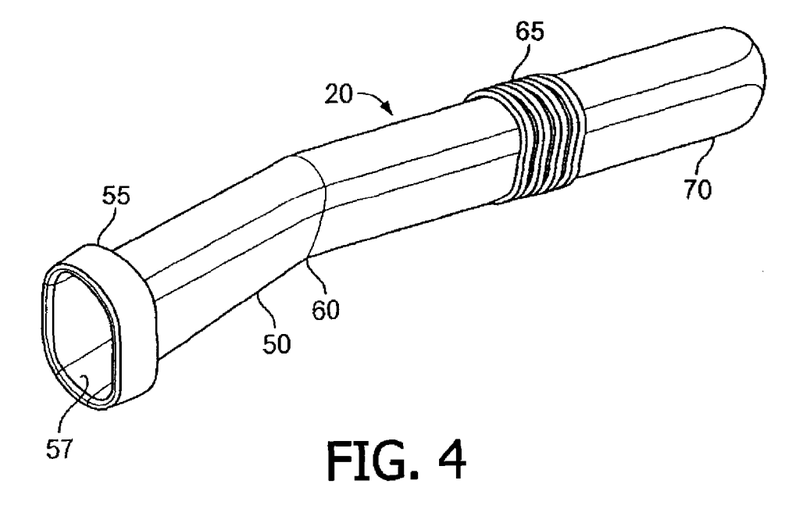
FIG. 4 is a three-dimensional view of the disposable insert depicted in FIG. 3.
Figure 5:
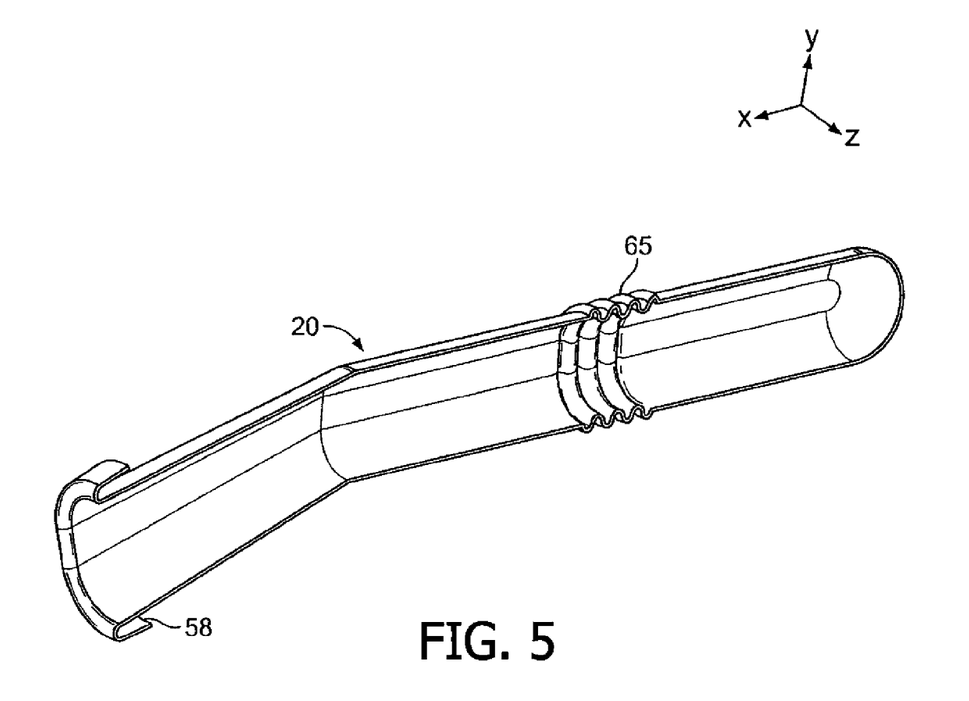
FIG. 5 is a cross-sectional three-dimensional view of the disposable insert depicted in FIGS. 3 and 4.

Referring now to FIGS. 3, 4 and 5, the removable and disposable insert 20, like the holder 30, has three regions or ends: a proximal region 50, a medial region 60, and a distal region 70. The insert 20 forms a hollow tube that is closed at its distal region 70. The proximal region 50 of the insert 20 forms an opening 57 through which the aspirator instrument 10 can be inserted into the insert 20. The medial region 60 forms a transition between the proximal and distal regions. The medial region 60 can form a bend that results in the proximal region 50 being at an angle $\theta^1$ relative to the distal region 70.

In other words, a longitudinal axis of the proximal region 50 is at an angle $\theta^1$ relative to the longitudinal axis of the distal region 70. The angle $\theta^1$ can be designed to be substantially complementary to a given type of aspirator instrument, such as the Yankauer tip mouthpiece instrument 10. In one embodiment, the angle $\theta^1$ is between about 0 degrees and about 12 degrees. In another embodiment, the angle $\theta^1$ is between about 12 degrees and about 16 degrees. In another embodiment, the angle $\theta^1$ is between about 13 degrees and about 15 degrees. In another embodiment, the angle $\theta^1$ is about 14 degrees. In another embodiment, the angle $\theta^1$ is greater than 16 degrees. Furthermore, the angle $\theta^1$ can be substantially complementary to the angle θ formed by the medial region 40 of the holder 30.

The proximal region 50 of the removable and disposable insert 20 has a proximal end that forms a lip 55. The lip 55 folds down a distance toward the medial and distal regions or ends of the insert 20. The lip can have a circumference and shape that is complementary to the proximal region or end 35 of the holder 30. The insert 20 can be supported by the interface between the top edge 38 of the holder 30 and the bottom surface 58 of the lip 55. Accordingly, the insert 20 can be easily removed from the holder 30 by pulling or pushing up on the top lip 55 of the insert 20.

The insert 20 also optionally has one or more accordion pleats 65 defined along a portion of the distal region 70 of the insert 20. The insert 20 can have one, two, three, four, five, or more accordion pleats 65 in its distal region 70. The accordion pleats 65 allow the distal region of the insert 20 to bend as needed to accommodate the size and shape of the aspirator instrument 10 being used.

Figure 6:
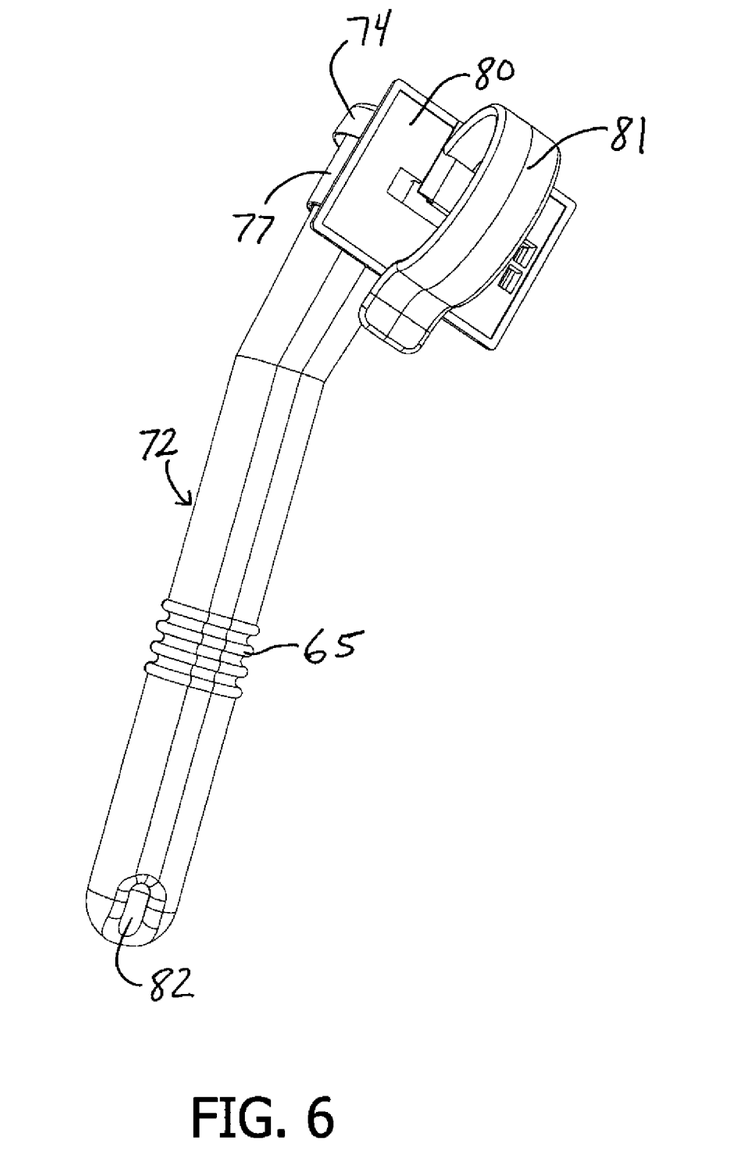
FIGS. 6 and 7 are perspective views of a disposable holster including a pinch that provides internal instrument supports.
Figure 7:
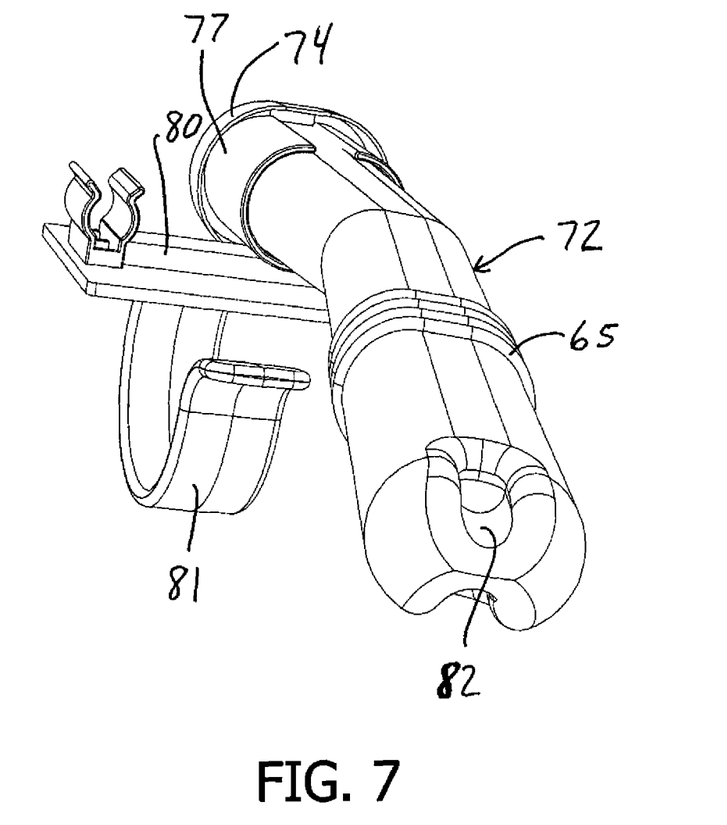

In another embodiment, as illustrated in FIGS. 6 and 7, a holster 72, similar to the insert 20, is attachable to a clip 80 or other fastener (collectively referred to hereinafter as a "clip," for ease of reference) via a top lip 74 on the proximal region of the holster 72. The top lip 74 optionally slides over an outwardly protruding attachment piece 77 on the clip 80. A separate holder 30 is not required to house the holster 72, which is preferably disposable. The holster 72 may include one or more pleats 65, a bend, or any other features that are optionally included on the insert 20.

The clip 80 is attachable to a bedrail, ventilator, hospital stand, wall, or other suitable object. As illustrated in FIGS. 6 and 7, the clip 80 optionally includes an arm 81 defining an opening that allows the arm 81 to slide over a bedrail. The clip 80 may additionally or alternatively include one or more tie-straps for tying the clip 80 to an object, or may include an adhesive surface or pad for adhering the clip 80 to a wall or other object, or may include any other suitable attachment mechanism.

Figure 8:
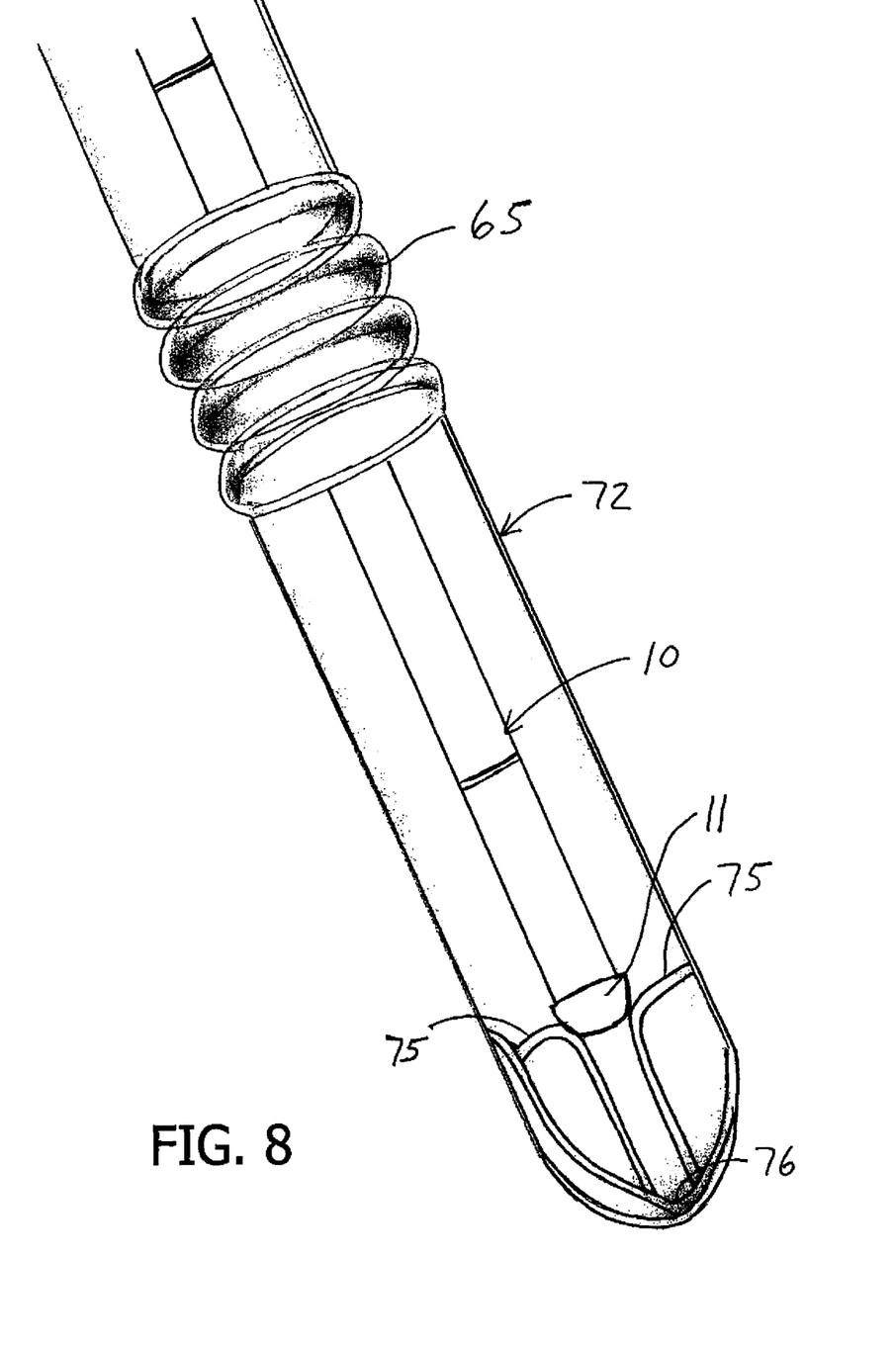
FIG. 8 is a partial perspective transparent view of the holster of FIGS. 6 and 7 showing the instrument supports supporting an instrument.

In one embodiment, as is best shown in FIG. 8, the holster 72 or insert 20 includes one or more upwardly projecting ledges 75, or upright supports, or horizontal supports, located at an interior area of its distal region (the holster is optionally at least partially transparent, as shown in FIG. 8). The one or more ledges 75 are used to support the tip 11 of an instrument 10 above a base region 76 of the holster 72 or insert 20. The one or more ledges 75 may be formed as part of the insert 20 or holster 72 itself, such as a "pinch" 82 of opposing walls of the closed end of the insert 20 or holster 72, or they may be one or more separate pieces adhered to or otherwise affixed to the interior of the insert 20 or holster 72. When the distal region includes a pinch 82, as shown in FIGS. 6-8, the pinch 82 forms two upwardly projecting ledges 75 upon which the instrument 10 may rest.

When an instrument 10 is loaded into the insert 20 or holster 72, the tip 11 of the instrument 10 comes to rest on the one or more ledges 75. As a result, fluids and secretions on the instrument 10 may drip off of the tip 11 and collect in the base region 76. This is advantageous because the instrument 10 rests above, not within, any unsanitary fluid collected in the insert 20 or holster 72. Accordingly, including one or more instrument supports in the insert 20 or holster 71 promotes sanitary conditions.

While several embodiments have been shown and described, various changes and substitutions may of course be made, without departing from the spirit and scope of the invention. The invention, therefore, should not be limited, except by any claims and their equivalents.

What is claimed is:

1. A system comprising:
   an instrument comprising a body cavity aspirator, the instrument having a distal most edge that forms a first convex surface;
   a holster comprising a substantially longitudinal body defining an interior for receiving the instrument, with the body including a distal region having a closed end portion and a proximal region having an opening for receiving the instrument, wherein a longitudinal axis of the proximal region is at an angle relative to a longitudinal axis of the distal region;
   an instrument support in the distal region for supporting the instrument in a position above the closed end portion, wherein the instrument support comprises at least two opposing walls of the distal region pinched inwardly to form at least two ledges, and wherein the instrument support is configured to prevent the instrument from contacting the closed end portion regardless of the orientation of the instrument, wherein the instrument support is a second convex surface that forms a cavity in the closed end portion, wherein the first and second convex surfaces face one another such that the second convex surface opposes and contacts the first convex surface of the distal most edge of the instrument when the instrument is positioned inside the instrument support so as to suspend the distal most edge over the cavity and prevent the distal most edge from contacting the closed end portion;
   a pleat on a distal region of the body.

2. The system of claim 1 wherein the instrument support further comprises at least one support piece adhered to the interior of the distal region of the body and projecting upwardly from the closed end portion.

3. The system of claim 1 further comprising a fastener for removably attaching the holster to an object, wherein the proximal region of the body is removably attachable to the fastener.

4. The system of claim 3 wherein the proximal region of the body includes a lip that is slidable over an attachment piece on the fastener.

5. The system of claim 3 wherein the fastener comprises a clip.

6. The system of claim 3 wherein the fastener includes an arm having an opening for sliding over a bedrail or other object.

7. The system of claim 3 wherein the fastener includes at least one tie-strap for securing the fastener to an object.

8. The system of claim 3 wherein the fastener includes an adhesive surface for adhering the fastener to an object.

* * * * *